United States Patent
Eck et al.

(10) Patent No.: US 6,700,016 B1
(45) Date of Patent: Mar. 2, 2004

(54) METHOD OF PURIFYING AND PRODUCING ACRYLIC ACID OR METHACRYLIC ACID

(75) Inventors: Bernd Eck, Viernheim (DE); Jörg Heilek, Bammental (DE); Dieter Baumann, Walldorf (DE); Volker Schliephake, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,711

(22) PCT Filed: May 31, 2000

(86) PCT No.: PCT/EP00/05004

§ 371 (c)(1), (2), (4) Date: Dec. 6, 2001

(87) PCT Pub. No.: WO00/75097

PCT Pub. Date: Dec. 14, 2000

(30) Foreign Application Priority Data

Jun. 8, 1999 (DE) .......................................... 199 26 082

(51) Int. Cl.$^7$ .............................................. C07C 51/42
(52) U.S. Cl. ...................................................... 562/600
(58) Field of Search ......................................... 562/600

(56) References Cited

U.S. PATENT DOCUMENTS 5,510,558 A  4/1996  Umansky et al.

FOREIGN PATENT DOCUMENTS

| CA | 2259945 | * 1/1998 |
|---|---|---|
| CN | 1105352 | 7/1995 |
| DE | 1 205 502 | 6/1966 |
| DE | 1 962 431 | 6/1970 |
| DE | 2 251 364 | 5/1973 |
| DE | 29 43 707 | 5/1980 |
| DE | 195 08 558 | 9/1996 |
| DE | 196 27 847 | 1/1998 |
| DE | 197 40 252 | 3/1999 |
| DE | 198 33 049 | 1/2000 |
| EP | 0 058 927 | 9/1982 |
| EP | 0 092 097 | 10/1983 |
| EP | 0 117 146 | 8/1984 |
| EP | 0 257 565 | 3/1988 |
| EP | 0 293 224 | 11/1988 |
| EP | 0 253 409 | 11/1991 |
| EP | 0 974 574 | 1/2000 |
| GB | 1 450 986 | 9/1976 |
| WO | WO 98/01415 | 1/1998 |

OTHER PUBLICATIONS

The Merck Index, 13$^{th}$ ed. pp. 24, 25 and 1062, Merck & Co., Inc. Whitehouse Station, NJ (2001).*

* cited by examiner

Primary Examiner—Mukund J. Shah
Assistant Examiner—Zachary C. Tucker
(74) Attorney, Agent, or Firm—Oblon, Spivak, McClelland, Maier & Neustadt, P.C.

(57) ABSTRACT

Acrylic acid or methacrylic acid is purified be crystallization to obtain crystals and a mother liquor, by a process in which the crystals are washed with a was liquid containing the acid and having a temperature from 15 to 40° C. Furthermore, a process for the preparation of acrylic acid or methacrylic acid comprises the abovementioned purification process.

21 Claims, No Drawings

METHOD OF PURIFYING AND PRODUCING ACRYLIC ACID OR METHACRYLIC ACID

This Application was filed under 35 U.S.C. 371 and is the U.S. National Stage of PCT/EP00/05004, filed May 31, 2000.

The present invention relates to a process for the purification of acrylic acid or methacrylic acid. The present invention furthermore relates to a process for the preparation of acrylic acid or methacrylic acid using the purification process.

Acrylic acid and methacrylic acid are key chemicals. Owing to their very reactive double bond and the acid function, acrylic acid is particularly suitable as a monomer for the preparation of polymers, for example for adhesives, dispersions, coating materials or superabsorbers.

WO-A-9 801 415 discloses a process for the preparation of acrylic acid or methacrylic acid, in which first a product mixture containing the acid is prepared, said mixture is condensed and the acid is then crystallized from the solution obtained in the condensation.

It is an object of the present invention to increase the purity of acrylic acid or methacrylic acid.

We have found that this object is achieved if the crystals of acrylic acid or methacrylic acid are washed with a wash or purification liquid containing the corresponding acid and having a temperature of from 15 to 40° C. Surprisingly, it has been found that a very good purification effect is achieved in a very simple manner by this measure.

The present invention therefore relates to a process for the purification of acrylic acid or methacrylic acid by crystallization to obtain crystals and a mother liquor, wherein the crystals are washed with a wash liquid containing acrylic acid or methacrylic acid and having a temperature of from 15 to 40° C.

In one embodiment, the present invention;relates to a process for the preparation of acrylic acid, which comprises the following stages:
 (a) preparation of a gaseous product mixture which essentially has the composition of a reaction mixture of the catalytic gas-phase oxidation of C3- or C4-alkanes, C3- or C4-alkenes, C3- or C4-alkanols and/or C3- or C4-alkanals and/or precursors thereof to acrylic acid or methacrylic acid,
 (b) condensation of the gaseous product mixture,
 (c) crystallization of the acrylic acid or methacrylic acid from the solution obtained in stage (b) and
 (d) purification of the acrylic acid or methacrylic acid from the crystals of the preceding stage according to the purification process of the invention described above.

Preferred embodiments of the invention are defined in the following description, the example and the subclaims.

According to the invention, the acrylic acid or methacrylic acid crystals are washed with a wash liquid or purification liquid containing the corresponding acid and having a temperature of from 15 to 40° C., preferably from 20 to 35° C., in particular from 20 to 30° C., most preferably from 20 to 25° C.

A wash liquid which has a higher purity than the mother liquor from the crystallization with respect to the acrylic acid or methacrylic acid to be crystallized is expediently used. Preferably, the wash liquid contains from 90 to 99.99, in particular from 97.0 to 99.9, most preferably from 99.0 to 99.8, % by weight, based in each case on 100% by weight of wash liquid, of acid. Pure acid, i.e. a pure product comprising from 99.3 to 99.8% by weight of acrylic acid or methacrylic acid, or the acid solution to be purified by crystallization, i.e. the feed of the crystallization or the solution obtained from the condensation of the gaseous product mixture according to stage (b), is advantageously used as wash liquid. The impurities in the wash liquid are generally impurities/byproducts from the preparation and/or purification process of the acid. The wash liquid is preferably used in an amount of from 3 to 80, in particular from 5 to 50, more preferably from 10 to 25, g of wash liquid/100 g of crystals.

The procedure for the wash process is not subject to any restriction. The washing can be carried out in one stage or in a plurality of stages. It is preferably carried out in a plurality of stages, in particular two stages. The washing can be effected continuously or batchwise in apparatuses customary for this purpose. Centrifuges, suction filters or belt filters are advantageously used. Expediently, washing is effected continuously with the use of continuous apparatuses for solid-liquid separation, such as centrifuges, decanters or belt filters, and batchwise with the use of batchwise apparatuses for solid-liquid separation, e.g. suction filters. The washing can be carried out on centrifuges or belt filters in one stage or a plurality of stages. Here, the wash liquid can also be fed countercurrently to the crystal cake.

In general, mixtures which preferably contain from 65 to 99.9, in particular from 75 to 99,8, most preferably from 85 to 99,5, % by weight, based in each case on 100% by weight of mixture, of acrylic acid or methacrylic acid, the remainder comprising impurities/byproducts of any type, in particular impurities or byproducts from the preparation process of the acid, for example of the catalytic gas-phase oxidation, are suitable for the crystallization of the acrylic acid or methacrylic acid, from which the crystals to be purified according to the invention are then obtained. The crystallization is advantageously carried out as a suspension crystallization.

The crystallization process used is not subject to any restriction. The crystallization can be carried out continuously or batchwise, in one stage or a plurality of stages. The crystallization is preferably effected in one stage. In another preferred embodiment of the invention, the crystallization is carried out as a fractional crystallization. In fractional crystallization, all stages which produce crystals which are purer than the acid solution fed in are usually referred to as purification stages and all other stages are usually referred to as stripping stages. Multistage processes are expediently operated here according to the countercurrent principle, in which, after the crystallization in each stage, the crystals are separated from the mother liquor and these crystals are fed to the respective stage having the next highest purity, while the crystallization residue is fed to the respective stage having the next lowest purity.

The temperature of the solution during the crystallization is advantageously from 14 to −30° C., in particular from 14 to −5° C. The solids content in the crystallizer is advantageously between 0 and 90, preferably between 10 and 80, more preferably between 15 and 50, g of solid/100 g of suspension.

In an advantageous embodiment of the invention, the crystallization is effected by cooling the apparatus walls or by evaporating the solution under reduced pressure. In the crystallization by cooling of apparatus walls, the heat is removed by means of scraped-wall heat exchangers which are connected to a stirred kettle or a container without a stirrer. The circulation of the crystal suspension is ensured here by a pump. In addition, it is also possible to remove the heat via the wall of a stirred kettle having a stirrer passing close to the wall. A further preferred embodiment in the case of the cooling crystallization comprises the use of cooling disk crystallizers, as produced, for example, by Gouda (the Netherlands). In a further variant of the crystallization by cooling, the heat is removed by means of conventional heat exchangers (preferably tube-bundle or plate-type heat exchangers). In contrast to scraped-wall heat exchangers, stirred kettles having stirrers passing close to the wall or cooling disk crystallizers, these apparatuses have no means for avoiding crystal layers on the heat-transfer surfaces. If a state in which the thermal resistance assumes too high a value owing to the formation of a crystal layer is reached during operation, switching to a second apparatus takes place. During the operating time of the second apparatus, the first apparatus is regenerated (preferably by melting off the crystal layer or flushing the apparatus with unsaturated solution). If too high a thermal resistance is reached in the second apparatus, switching back to the first apparatus takes place, etc. This variant can also be operated with more than two apparatuses cyclically. Moreover, the crystallization can be carried out by conventional evaporation of the solution under reduced pressure.

After the crystallization, the acid crystals obtained are expediently separated from the mother liquor. The method for carrying out the separation is not subject to any particular restrictions. All known solid-liquid separation methods are suitable. In one embodiment, the crystals are separated from the mother liquor by filtration and/or centrifuging. Advantageously, the filtration or centrifuging is preceded by preliminary thickening of the suspension, for example by hydrocyclone(s). All known centrifuges which operate batchwise or continuously are suitable for the centrifuging. Reciprocating-conveyor centrifuges which can be operated in one stage or a plurality of stages are most advantageous. Helical screen centrifuges or helical conveyor centrifuges (decanters) are also suitable. Filtration is advantageously effected by means of suction filters which are operated batchwise or continuously, with or without a stirrer, or by means of belt filters. In general, the filtration can be effected under superatmospheric pressure or reduced pressure. It is also possible to provide sweating of the crystals or of the crystal cake in addition to the wash process according to the invention. Said sweating comprises local melting of impure regions. The sweating is preferably carried out on centrifuges or belt filters.

The purification according to the invention process is advantageously carried out using crystals which contain from 85 to 99.9, in particular from 95 to 99.5, % by weight, based in each case on 100% by weight of crystals, of acid. Regarding impurities or by products, the crystals, mainly contain those which originate from the preparation and/or purification of the crude acid. The acid crystals obtained after carrying out the purification process according to the invention contain as a rule from 95 to 99.9, in particular from 99.0 to 99.8, more preferably from 99.3 to 99.8, % by weight, based on 100% by weight of acid crystals, of acid.

The purification process according to the invention permits a significant increase in the purity by from 20 to 70%, depending on impurity component and based on the unwashed crystals, in a simple manner by washing the crystals.

In one embodiment, the present invention relates to a process for the preparation of acrylic acid or methacrylic acid which comprises the stages (a) to (d) defined above.
Stage (a):

In stage (a), a gaseous product mixture %which essentially has the composition of reaction mixture of the catalytic gas-phase oxidation of C3- or C4-alkanes, C3- or C4-alkenes, C3- or C4-alkanols and/or C3- or C4-alkanals and/or precursors thereof to acrylic acid or methacrylic acid is prepared. The gaseous product mixture is particularly advantageously prepared by catalytic gas-phase oxidation of propene, acrolein, tert-butanol, isobutene, isobutane, isobutyraldehyde, methacrolein, isobutyric acid or methyl tert-butyl ether. The starting compounds used may be all precursors of said compounds, in which the actual C3/C4 starting compound forms only as an intermediate during the gas-phase oxidation. Methyl tert-butyl ether or isobutyric acid may be mentioned by way of example for the preparation of methacrylic acid.

The catalytic gas-phase reaction of propene and/or acrolein with molecular oxygen to give acrylic acid by known processes, in particular as described in DE-A-1 962 431, DE-A-2 943 707, DE-C-1 205 502, DE-A-195 08 558, EP-A-0 257 565, EP-A-0 253 409, DE-A-2 251 364, EP-A-0 117 146, GB-B-1 450 986 and EP-A-0 293 224, is particularly advantageous. Here, temperatures between 200 and 450° C. and, if required, superatmospheric pressure are preferably employed. Preferably used heterogeneous catalysts are oxidic multicomponent catalysts based on the oxides of molybdenum, bismuth and iron in the 1st stage (oxidation of propene to acrolein) and those based on the oxides of molybdenum and vanadium in the 2nd stage (oxidation of acrolein to acrylic acid). If propane is used as the starting material, it can be converted into a propene/propane mixture by: catalytic oxydehydrogenation, as described, for example, in Catalysis Today 24 (1995), 307 to 313 or U.S. Pat. No. 5,510,558; by homogeneous oxydehydrogenation, as described, for example, in CN-A 1 105 352; or by catalytic dehydrogenation, as described, for example, in EP-A 0 253 409, EP-A 0 293 224, DE-A 195 08 558 or EP-A 0 117 146. When a propene/propane mixture is used, propane acts as a diluent gas. Other suitable propene/propane mixtures are refinery propene (70% of propene and 30% of propane) or cracker propene (95% of propene and 5% of propane). In principle, propene/propane mixtures such as those mentioned above can be oxidized with oxygen or air or a mixture of oxygen and nitrogen of any composition to give acrolein and acrylic acid.

The conversion of propene to acrylic acid is highly exothermic. The reaction gas, which advantageously contains an inert diluent gas, e.g. atmospheric nitrogen, one or more saturated C1–C6-hydrocarbons, in particular methane and/or propane, and/or steam, in addition to the starting materials and products, can therefore take up only a small part of the heat of reaction. Although the type of reactors used is not subject to any restriction per se, tube-bundle heat exchangers which are filled with the oxidation catalyst are generally used since in them the predominant part of the heat liberated during the reaction can be removed by convection and radiation to the cooled tube walls.

Catalytic gas-phase oxidation gives not pure acrylic acid but a gaseous mixture which, in addition to the acrylic acid, may contain essentially unconverted acrolein and/or propene, steam, carbon monoxide, carbon dioxide, nitrogen, propane, oxygen, acetic acid, propionic acid, formaldehyde, further aldehydes and maleic anhydride as secondary components. Usually, the reaction product mixture contains from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride, and from 20 to 98, preferably from 50 to 98, % by weight of inert diluent gases, based in each case on the total reaction mixture. In particular, saturated C1–C6-hydrocarbons, such as from 0 to 90% by weight of methane and/or propane, as well as from 1 to 30% by weight of steam, from 0.05 to 15% by weight of oxides of carbon and from 0 to 90% by weight of nitrogen, based in each case on 100% by weight of diluent gas, are present as inert diluent gases.

Methacrylic acid can be prepared analogously to acrylic acid by catalytic gas-phase reaction of C4 starting compounds with molecular oxygen. Methacrylic acid is particularly advantageously obtainable, for example, by catalytic gas-phase oxidation of isobutene, isobutane, tert-butanol, isobutyraldehyde, methacrolein or methyl tert-butyl ether. The catalysts used are likewise transition metal mixed oxide catalysts (e.g. Mo, V, W and/or Fe). Particularly suitable processes are those in which the preparation is carried out starting from methacrolein, in particular when the methacrolein is produced by gas-phase catalytic oxidation of tertbutanol, isobutane or isobutene or by reaction of formaldehyde with propionaldehyde according to EP-B 0 092 097 or EP-B 0 058 927. It is thus also possible to prepare methacrylic acid in two stages by (1) condensation of propionaldehyde with formaldehyde (in the presence of a secondary amine as catalyst) to give methacrolein and (2) subsequent oxidation of the methacrolein to methacrylic acid.

As in the preparation of acrylic acid, the product is not pure methacrylic acid but a gaseous mixture which, in addition to the methacrylic acid, may contain essentially unconverted methacrolein and/or steam, carbon monoxide, carbon dioxide, nitrogen, oxygen, acetic acid, propionic acid, further aldehydes and maleic anhydride as secondary components. The process according to the invention is used in particular when the reaction mixture contains from 0.02 to 2% by weight, based on the total reaction mixture, of methacrolein and otherwise essentially the same corresponding components as in the preparation of acrylic acid.

Stage (b):

In stage (b), the reaction product obtained in stage (a) is subjected to a condensation, in particular a partial or total condensation, a solution being obtained. The condensation can be effected by conventional methods in one stage or a plurality of stages, and the type of condensation is not subject to any particular restriction. Advantageously, the condensation is carried out using a direct condenser, condensate already produced being brought into contact with the hot gaseous reaction product. Suitable apparatuses for the condensation are in particular spray-type scrubbers, Venturi scrubbers, bubble columns or apparatuses having sprayed surfaces.

The mixture obtained by partial or total condensation of the reaction product from stage (a) preferably contains from 65 to 99.5% by weight of acrylic acid or methacrylic acid, from 0.1 to 35% by weight of water and furthermore from 0.1 to 15% by weight of impurities, in particular, based in each case on 100% by weight of condensate, from 0.01 to 5% by weight of acrolein or methacrolein, from 0.05 to 5% by weight of acetic acid, from 0.01 to 5% by weight of propionic acid, from 0.01 to 5% by weight of formaldehyde, from 0.01 to 5% by weight of further aldehydes and from 0.01 to 5% by weight of maleic acid. Particularly preferably, a mixture which contains from 85 to 99.5, in particular from 90 to 98.5, % by weight of acrylic acid or methacrylic acids from 0.1 to 15, in particular form 0.5 to 10, % by weight of water and furthermore from 0.5 to 5% by weight of impurities, in particular, based in each case on 100% by weight of condensate, from 0.01 to 3% by weight of acrolein or methacrolein, from 0.5 to 3% by weight of acetic acid, from 0.01 to 3% by weight of propionic acid, from 0.01 to 3% by weight of formaldehyde, from 0.01 to 3% by weight of further aldehydes and from 0.01 to 3% by weight of maleic acid, is obtained during the condensation.

Stage (c):

In stage (c), the solution obtained in stage (b) and containing acrylic acid or methacrylic acid is crystallized. Thus, the solution obtained in the condensation stage is fed directly to the crystallization. Here, the procedure is carried out without the addition of a solvent, in particular without the addition of an organic solvent.

The crystallization is preferably carried out as described above, crystals and mother liquor being obtained.

Stage (d):

In stage (d), after separation of the mother liquor, which is carried out as described above, the crystals of the preceding stage are washed according to the purification process according to the invention, in order to obtain the purified acrylic acid or methacrylic acid.

Thus, the present invention provides a process for the preparation and purification of acrylic acid or methacrylic acid in which a significant increase in the purity of the desired acid is achieved by a simple purification method.

The Example which follows illustrates the invention and constitutes a preferred embodiment of the invention.

EXAMPLE

A crude acrylic acid having the composition stated in Table 1 below was crystallized continuously at a temperature 9.4° C. by cooling crystallization in a cooling disk crystallizer (100 l). The solids content in the crystallizer was 28 g of solid/100 g of suspension.

TABLE 1

| Composition of the crude acrylic acid to be crystallized: | | |
|---|---|---|
| Acrylic acid | 96.43 | % by weight |
| Acetic acid | 0.84 | % by weight |
| Propionic acid | 610 | ppm |
| Furan(II)aldehyde | 0.41 | % by weight |
| Benzaldehyde | 240 | ppm |
| Maleic acid | 200 | ppm |
| Allyl acrylate | 0.22 | % by weight |
| Water | 1.43 | % by weight |
| Others | 0.565 | % by weight |

After the crystallization, the acrylic acid was separated from the mother liquor on a two-stage reciprocating-conveyor centrifuge (diameter 400 mm, speed 1900 rpm) with countercurrent washing. The amount of wash liquid was 25 g of wash liquid/100 g of crystal cake. The composition of the wash liquid was as follows:

TABLE 2

| Composition of the wash liquid | | |
|---|---|---|
| Acrylic acid | 99.67 | % by weight |
| Acetic acid | 1333 | ppm |
| Propionic acid | 342 | ppm |
| Furan(II)aldehyde | 263 | ppm |
| Benzaldehyde | 85 | ppm |
| Maleic acid | 124 | ppm |
| Allyl acrylate | 54 | ppm |
| Water | 540 | ppm |
| Others | 587 | ppm |

Depending on the temperature of the wash liquid, the resulting composition of the crystals was that stated in Table 3. Here, all data, except for acrylic acid, are based on ppm, while the amount of acrylic acid is based on % by weight.

TABLE 3

Composition of the crystals as a function of the temperature of the wash liquid

|  | Without washing | 15° C. | 20° C. | 25° C. | 30° C. |
|---|---|---|---|---|---|
| Acrylic acid | 99.62 | 99.75 | 99.76 | 99.77 | 99.77 |
| Acetic acid | 1920 | 1504 | 1436 | 1422 | 1386 |
| Propionic acid | 219 | 189 | 189 | 182 | 174 |
| Furan(II)aldehyde | 281 | 139 | 118 | 94 | 94 |
| Benzaldehyde | 19 | 9 | 7 | <5 | <5 |
| Maleic acid | 18 | 7 | 6 | <5 | <5 |
| Allyl acrylate | 165 | 79 | 68 | 53 | 51 |
| Water | 510 | 261 | 248 | 241 | 241 |
| Others | 624 | 301 | 294 | 270 | 254 |

Thus, the washing of the crystal cake according to the invention leads to a significant increase in the purity of the acrylic acid.

We claim:

1. A process for the purification of acrylic acid by crystallization to obtain crystals and a mother liquor, wherein the crystals are washed with a wash liquid comprising acrylic acid and having a temperature of from 20 to 35° C.

2. A process as claimed in claim 1, wherein a wash liquid which has a higher purity than the mother liquor with respect to acrylic acid is used.

3. A process as claimed in claim 1, wherein a wash liquid comprising from 97.0 to 99.9% by weight, based on 100% by weight of liquid, of acrylic acid is used.

4. A process as claimed in claim 1, wherein the crystallization is carried out as a suspension crystallization.

5. A process as claimed in claim 1, wherein a wash liquid having a temperature of from 20 to 30° C. is used.

6. A process as claimed in claim 1, wherein a wash liquid having a temperature of from 20 to 25° C. is used.

7. A process as claimed in claim 1, wherein washing is effected with an amount of from 3 to 80 g of wash liquid/100 g of crystals.

8. A process as claimed in claim 1, wherein the wash liquid used is a pure product comprising from 99.3 to 99.8% by weight of acrylic acid.

9. A process as claimed in claim 1, wherein the washing is carried out in a plurality of stages.

10. A process for the preparation of acrylic acid by
 (a) preparation of a gaseous product mixture which essentially has the composition of a reaction mixture of the catalytic gas-phase oxidation of C3- or C4-alkanes, C3- or C4-alkenes, C3- or C4-alkanols and/or C3- or C4-alkanals and/or precursors thereof to acrylic acid,
 (b) condensation of the gaseous product mixture,
 (c) crystallization of the acrylic acid from the solution obtained in stage (b) and
 (d) purification of the acrylic acid from the crystals of the preceding stage by washing the crystals with a wash liquid comprising acrylic acid and having a temperature of from 20 to 35° C.

11. A process as claimed in claim 10, wherein in stage (d) a wash liquid which has a higher purity than the mother liquor with respect to acrylic acid is used.

12. A process as claimed in claim 10, wherein in stage (d) a wash liquid comprising from 97.0 to 99.9% by weight, based on 100% by weight of wash liquid, of acrylic acid is used.

13. A process as claimed in claim 10, wherein in stage (d) the crystallization is carried out as a suspension crystallization.

14. A process as claimed in claim 10, wherein in stage (d) a wash liquid having a temperature of from 20 to 30° C. is used.

15. A process as claimed in claim 10, wherein in stage (d) a wash liquid having a temperature of from 20 to 25° C. is used.

16. A process as claimed in claim 10, wherein in stage (d) washing is effected with an amount of from 3 to 80 g of wash liquid /100 g of crystals.

17. A process as claimed in claim 10, wherein in stage (d) the wash liquid used is a pure product comprising from 99.3 to 99.8% by weight of acrylic acid.

18. A process as claimed in claim 10, wherein in stage (d) the washing is carried out in a plurality of stages.

19. A process as claimed in claim 10, wherein the wash liquid is a solution obtained from the condensation of the gaseous product mixture in (b).

20. The process as claimed in claim 1, wherein the wash liquid comprises from 97.0 to 99.9% by weight, based on 100% by weight of wash liquid, of acrylic acid, the wash liquid having a temperature of from 20 to 25° C.

21. The process as claimed in claim 10, wherein the wash liquid comprises from 97.0 to 99.9% by weight, based on 100% by weight of wash liquid, of acrylic acid, said wash liquid having a temperature of from 20 to 25° C.

* * * * *